United States Patent [19]
Mahgerefteh et al.

[11] Patent Number: 6,072,308
[45] Date of Patent: *Jun. 6, 2000

[54] PARTICLE SIZE ANALYZER

[76] Inventors: Haroun Mahgerefteh; Ali Shaeri, both of 61 Broughton Avenue, Finchley, London N3 3EN, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/833,831

[22] Filed: Apr. 10, 1997

[30] Foreign Application Priority Data

Feb. 11, 1994 [GB] United Kingdom ............... 229477

[51] Int. Cl.⁷ ............... G01N 27/00; G01N 15/02
[52] U.S. Cl. ............... 324/71.1; 73/865.5; 209/233
[58] Field of Search ............... 324/71.1, 71.4; 209/237, 634, 669, 668, 664, 632, 233, 234, 239, 362; 131/290; 425/197; 356/336; 73/865.5

[56] References Cited

U.S. PATENT DOCUMENTS

| | | | |
|---|---|---|---|
| 4,022,638 | 5/1977 | Weet | 134/1 |
| 4,298,836 | 11/1981 | Groves | 324/71.1 |
| 5,059,310 | 10/1991 | Fischer | 209/237 |
| 5,245,290 | 9/1993 | Cannon | 324/457 |

OTHER PUBLICATIONS

T. Allen, "Particle Size Measurement", Fourth Edition 1990, Chapman and Hall, London)—cover page; Table of Contents; pp. 192–217, 248–251, 284–293, 310–311, 344–345, 372–373, 404–407, 454–461, 502–507, 540–541, 596–599, 624–625, 652–655, 682–737.

*Primary Examiner*—Josie Ballato
*Assistant Examiner*—Russell M. Kobert
*Attorney, Agent, or Firm*—Frishauf, Holtz, Goodman, Langer & Chick, P.C.

[57] ABSTRACT

The application describes a particle size analyser comprising a horizontally held close-coiled helical spring which is partly filled with the powder under test. The operation of the technique involves stretching the spring to various known lengths and vibrating it in the lateral direction at or around its first harmonic resonant frequency with a low amplitude of vibration. Measurements of the mass of the powder discharged from spring coils for a given spring extension and relating the latter to the particle size of the discharged powder by reference to a previously generated calibration curve provide data on the particle size distribution.

31 Claims, 6 Drawing Sheets

PARTICLE SIZE ANALYZER

BACKGROUND OF THE INVENTION

Heretofore, many devices of high sensitivity have been developed for particle size measurements. These either rely on direct dimensional measurement; sieving and microscopy or depend on physical response, i.e. electrozone, various light beam interference techniques or sedimentation. Most of these techniques are either time consuming, require expensive equipment or are capable of analysing small samples only. In addition, the majority are not suitable for on-line monitoring. This is an important drawback as in the manufacture, for example, of industrial powders as diverse as paint pigments, cement and photocopier toner, there is a requirement to control tightly the particle size distribution. An on-line capability allows immediate readjustment of the process parameters that control the particle size if and when required.

A recent review of the most widely used techniques for particle size analysis has been presented in a publication by T. Allen, "Particle Size Measurement", Fourth edition, 1990 (Chapman and Hall: London).

The aim of the present invention is to provide a new and improved particle size distribution analyser.

According to the present invention there is provided a particle size analyser comprising a horizontally held close-coiled helical spring, partly filled with the powder under test, means to stretch the spring along its length and means to measure its corresponding extension, means to vibrate the spring in a direction normal to its main axis at selected frequency and amplitude of vibration, and means to direct the discharged powder from the spring coils into a container for mass measurement.

SUMMARY OF THE INVENTION

The application describes a particle size analyser comprising a horizontally held close-coiled helical spring which is partly filled with the powder under test. The operation of the technique involves stretching the spring to various known lengths and vibrating it in the lateral direction at or around its first harmonic resonant frequency with a low amplitude of vibration. Measurements of the mass of the powder discharged from spring coils for a given spring extension and relating the latter to the particle size of the discharged powder by reference to a previously generated calibration curve provide data on the particle size distribution.

The invention provides several advantages as compared to existing devices for particle size measurement. For example, as a typical test sample used is relatively large (ca. 10 grams), the problems associated with the selection of representative samples are minimised. Other advantages include low manufacturing and maintenance costs together with simplicity and ease of use. In contrast to the majority of particle sizing techniques, no special sample preparation is required. In addition, as compared to sieving which is the most common way of particle size analysis, the proposed device provides a shorter analysis time. Finally, as the proposed device operates by physically separating the test sample into different size fractions, it may also be used as a classifier.

DESCRIPTION OF THE DRAWINGS

FIG. 2 shows the connection of the spring to the positioning plate which is in turn connected to the adjustable screw.

FIG. 3 illustrates the graduated scale.

FIG. 4 shows in perspective, three sides of the structural frame and one of the two slide rails connected to it.

FIG. 5 shows perspective and section views of the base disc incorporating a tapered groove leading to a discharge port machined at its centre.

FIG. 6 shows the sample collector.

DESCRIPTION OF THE INVENTION

Figure 1:
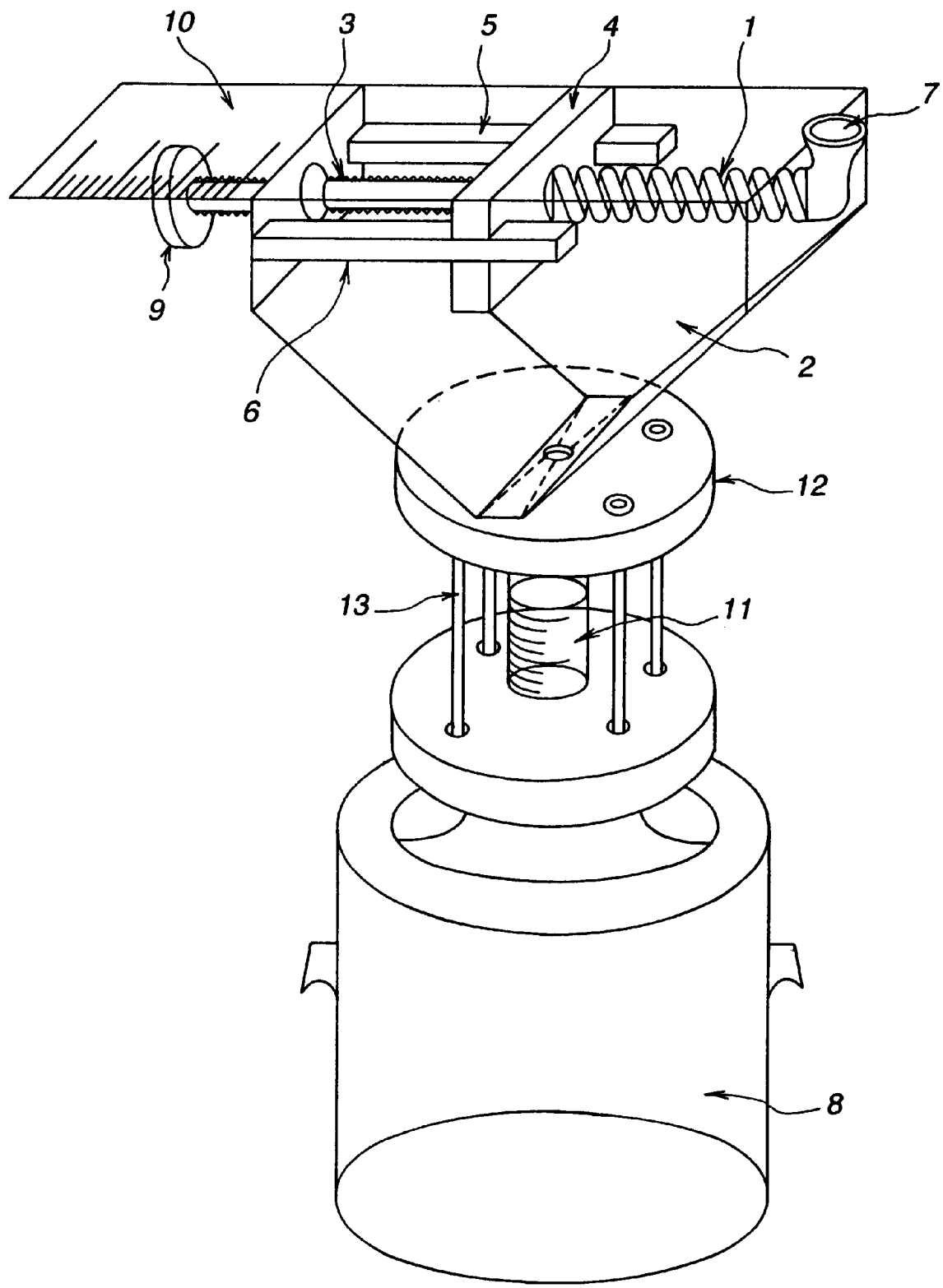
FIG. 1 shows in perspective, a schematic representation of a measurement device according to the invention.
Figure 2:
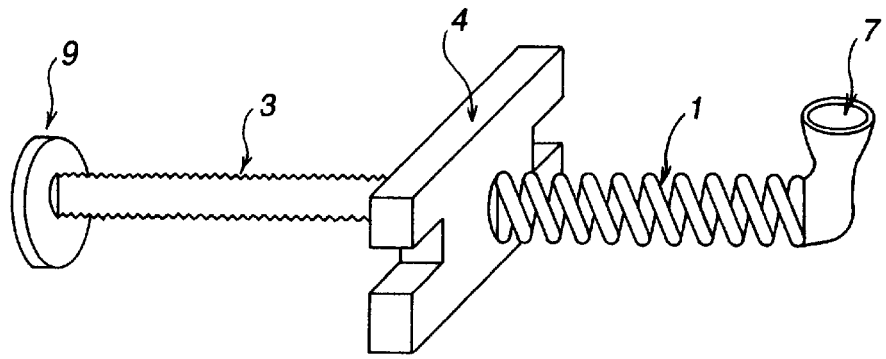
FIGS. 2–6 show the various components of the device in isolation where.
Figure 3:
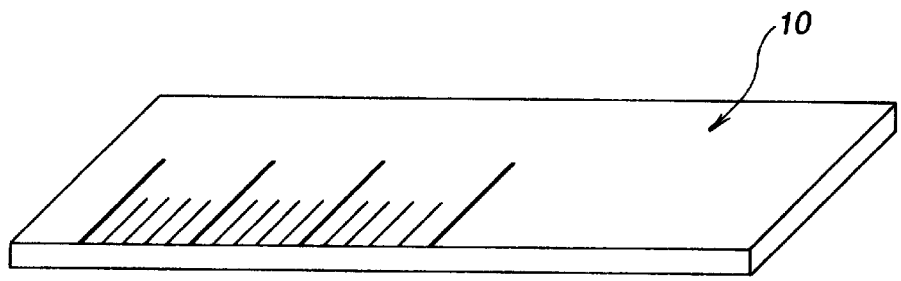
Figure 4:
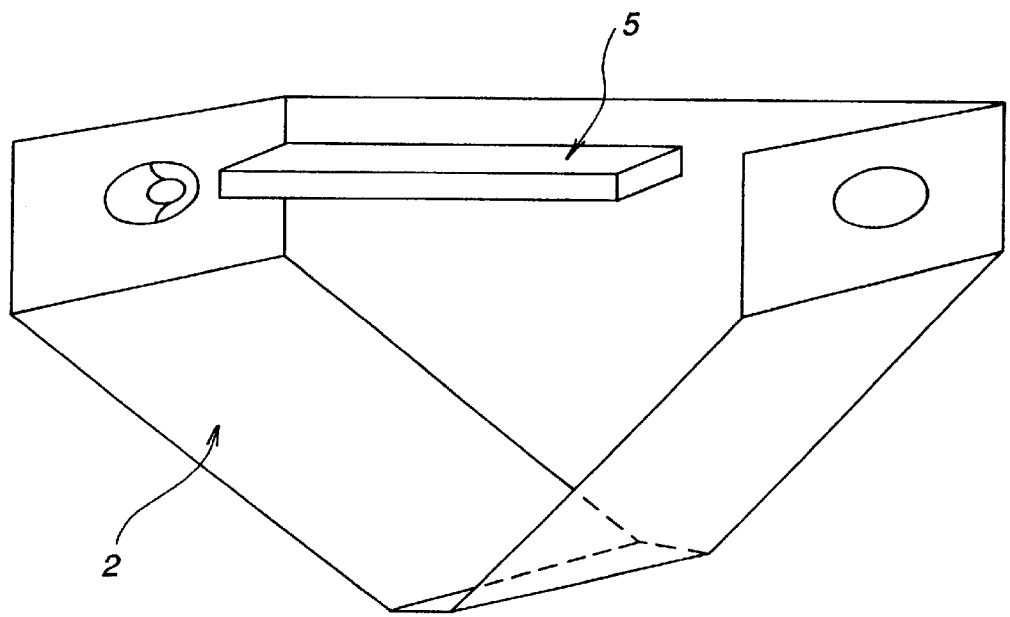
Figure 5:
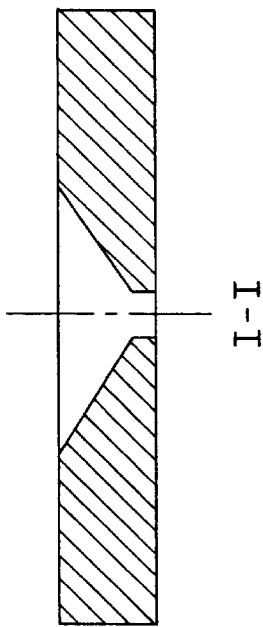
Figure 6:
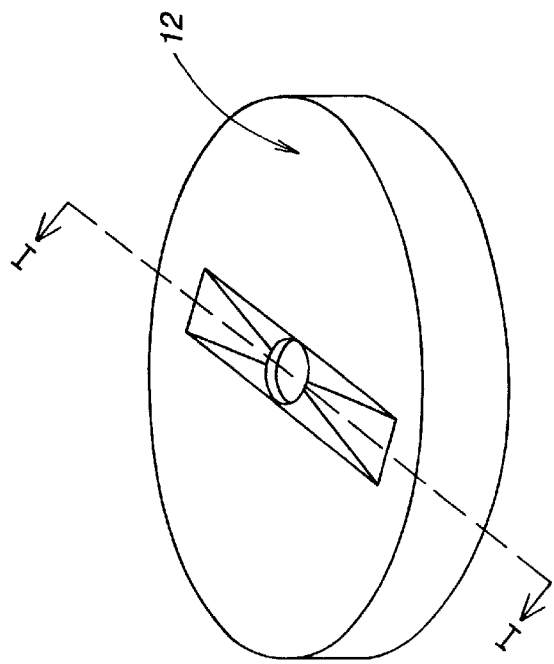

Referring to FIGS. 1–6, the particle sizer comprises a horizontally held close-coiled helical spring 1 with squared and ground ends, ca. 100 mm in length, 10 mm mean diameter made from 1 mm dia. steel wire. One end is securely attached to one side of a main chamber 2 whilst the other end, permanently sealed, is securely attached to a 100 mm long, M6×1.00 screw 3 via a positioning plate 4 mounted on two slide rails 5 and 6. A feed elbow 7, made from a suitable material such as a plastic is used to direct the test powder into the spring via a 10 mm hole drilled into the side of the main chamber.

The spring is stretched by turning the screw 3 which is also threaded into the wall of the chamber 2. The extension of the spring, accompanied by its vibration in the lateral direction using a standard electrodynamic vibration generator 8 results in the discharge of the test powder through the spring coils.

The inventors have found that when the spring is vibrated in the lateral direction at or around its first harmonic resonant frequency with a sufficiently low amplitude thus ensuring a small lateral deflection, the particle size of the discharged powder is linearly and accurately proportional to the spring longitudinal extension. This is in turn measured by reference to the location of the screw head 9 in relation to a graduated scale 10.

The main chamber 2 is suitably angled (ca. 40° to the horizontal) in order to direct the discharged powder into a sample collector 11 for mass measurement. A base disc 12 serves as the connection between the main chamber 2 and the sample collector 11. The base disc also incorporates a tapered rectangular notch machined at its centre which directs the discharged powder into the sample collector via a 10 mm dia threaded hole located at its centre.

The whole assembly is mounted on top of the vibration generator 8 using four supporting rods 13 in the manner shown in FIG. 1.

Particle size distribution of the test powder may be determined by plotting the particle size against the corresponding mass of the discharged powder collected in the sample collector 11. The sample mass may be obtained by un-screwing the sample collector from the base disc 12 and weighing.

Figure 7:
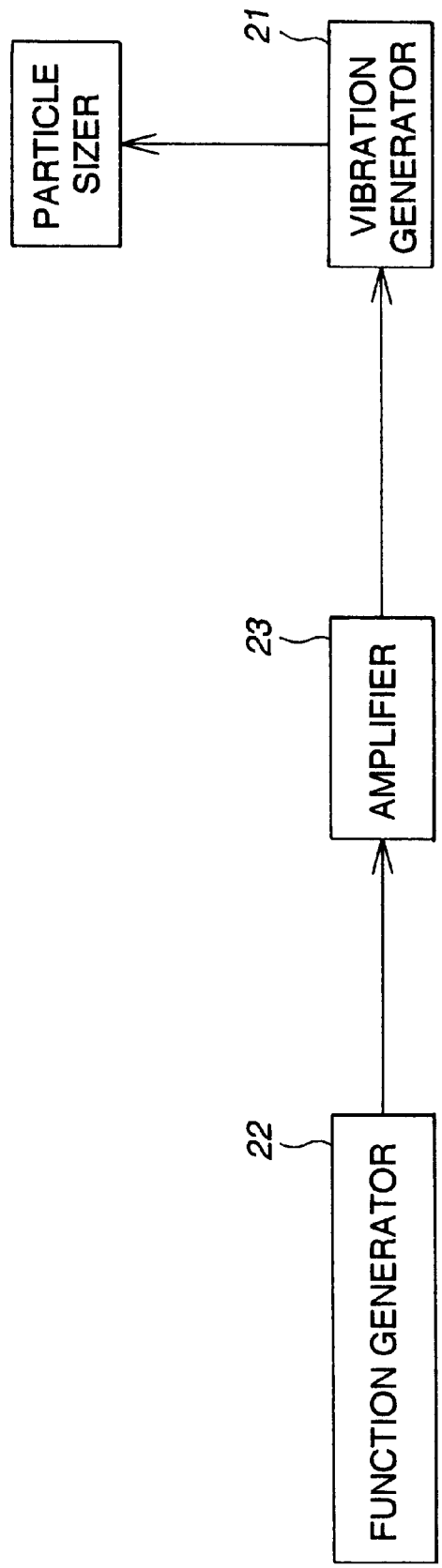
FIG. 7 is a schematic representation of the electronic drive configuration.

FIG. 7 is a schematic representation of the basic configuration of the electronic drive system. The electrodynamic vibration generator 21, is driven using a frequency function generator 22 (0.1 Hz–0.1 MHz range) via a variable gain 50 Watt power amplifier 23. The unit comprises two armature drive coils of differing impedance. These operate directly from the power amplifier. The vibrator has a rated peak sinusoidal force of 97.9 N corresponding to maximum displacement and acceleration of 7 mm and 50 g respectively.

Figure 8:
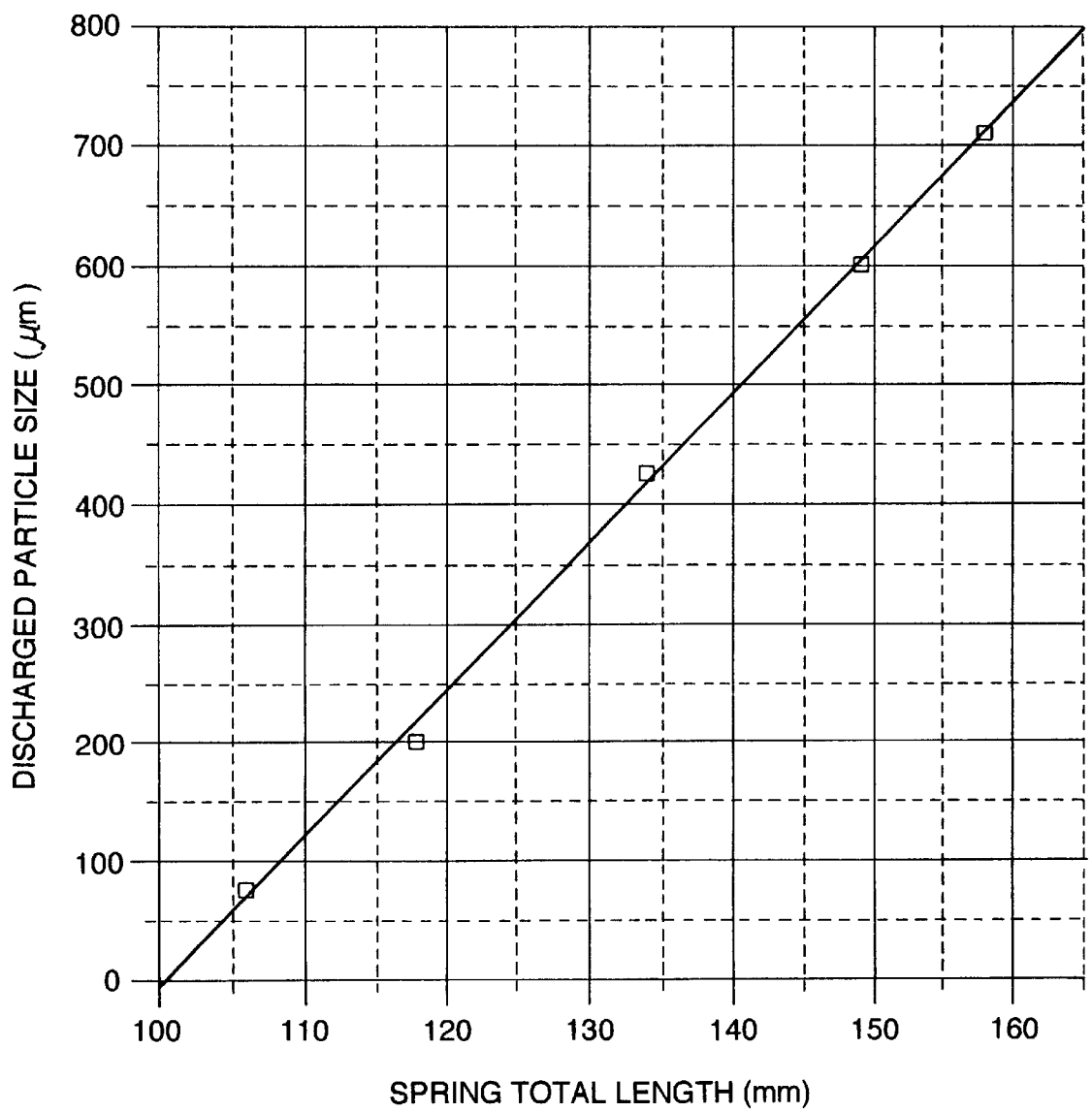
FIG. 8 is a calibration graph showing the variation of spring longitudinal extension against the particle size of the discharged powder.

FIG. 8 is a calibration graph showing the variation of spring length with particle diameter of the discharged powder. The data relate to a 6 gram sample of glass Ballotini vibrated at ca. 39 Hz and 5 Watt drive power. The test sample comprises sieve cuts in the ranges 0–75, 75–200, 200–425, 425–600, and 600–710 μm prepared in accordance to British Standards for Test Sieving (BS 1796: Part 1:1989).

The spring is also partly filled with some (ca 2 grams) relatively large (ca. 1000 μm) Ballotini particles. The inventors have found that this procedure produces better performance in terms of the response of the particle sizer by facilitating dispersion of the test particles and also by reducing the lateral amplitude of vibration of the spring.

The latter is important as during vibration, for a given spring extension along its length, any accompanied lateral deflection will result in the broadening of the size distribution of the discharged powder. It will also produce a non-linear response in terms of variation of spring longitudinal extension with particle size.

It is important to ensure that the maximum longitudinal extension of the spring is limited such that the large dispersing Ballotini spheres are always confined within the spring during tests.

Using the above configuration, the maximum vibration amplitude of the spring as measured at its centre using a travelling microscope is ca. 2 mm throughout the size analysis.

The data in FIG. 8 may be fitted to a straight line having a correlation coefficient of 0.99992.

Figure 9:
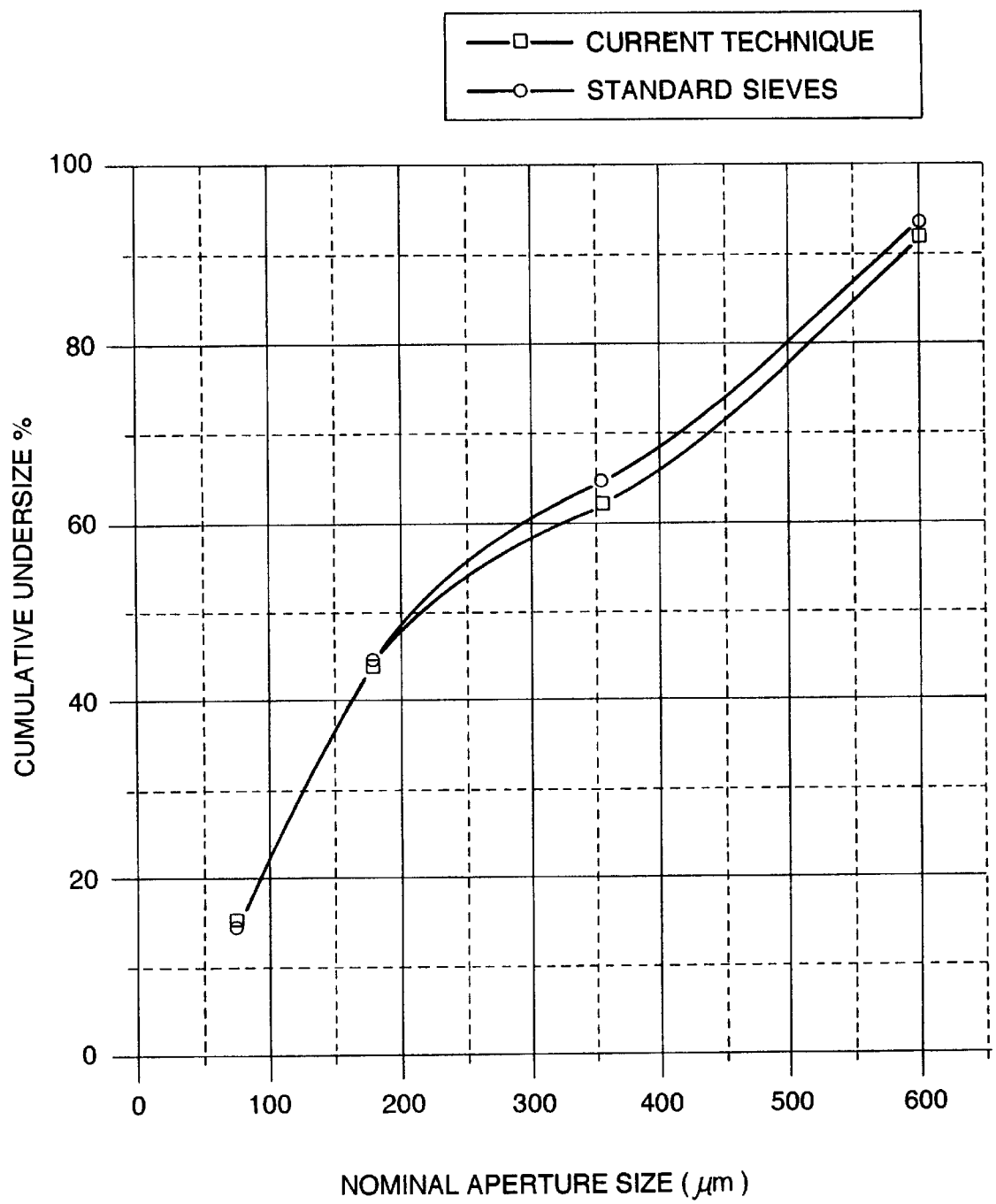
FIG. 9 is a graph showing a comparison between particle size distribution data obtained using the present invention and those produced using sieving.

FIG. 9 shows particle size distribution data, expressed in terms of % mass cumulative undersize vs. particle size using the present invention. The corresponding data produced using sieving are also included for comparison. The test sample is 6 grams of glass Ballotini. The total analysis time using the present invention is ca. 6 minutes as compared to 30 minutes using sieves. As it may be observed, the maximum discrepancy between the data produced using the two techniques is ca±2.6%.

We claim:

1. A particle size distribution analyzer comprising:
   a helical spring having a central cavity;
   a feed member for introducing a sample of a powder into the central cavity;
   means for extending a length of the spring by a predetermined amount;
   a vibration generator for vibrating the spring, after extension thereof, in a direction normal to the length of the spring and, thereby, to discharge at least some of the powder from the central cavity; and
   means for measuring the mass of the discharged powder.

2. A particle size distribution analyzer according to claim 1, wherein the means for measuring the mass of the discharged powder comprises means for collecting the discharged powder and means for weighing the collected powder.

3. A particle size distribution analyzer according to claim 1, wherein the means for measuring the mass of the discharged powder comprises means for measuring at least one vibration characteristic of the spring and means for determining the mass of powder remaining in the central cavity based on the at least one measured vibration characteristic.

4. A particle size distribution analyzer according to claim 3, wherein the means for measuring the mass of the discharged powder comprises means for measuring an amplitude of vibration of the spring.

5. A particle size distribution analyzer according to claim 4, wherein the means for measuring the mass of the discharged powder comprises a feedback circuit which includes the spring therein and which controls the vibration generator to vibrate the spring at a resonant frequency.

6. A particle size distribution analyzer according to claim 4, wherein the means for measuring the mass of the discharged powder comprises a manually tunable circuit for controlling the vibration generator to vibrate the spring at a resonant frequency.

7. A particle size distribution analyzer according to claim 3, wherein the means for measuring the mass of the discharged powder comprises means for measuring a resonant frequency of vibration of the spring.

8. A particle size distribution analyzer according to claim 7, wherein the means for measuring the mass of the discharged powder comprises a feedback circuit which includes the spring therein and which controls the vibration generator to vibrate the spring at the resonant frequency.

9. A particle size distribution analyzer according to claim 7, wherein the means for measuring the mass of the discharged powder comprises a manually tunable circuit for measuring a frequency of the vibrating spring at resonance.

10. A method of using the particle size distribution analyzer of claim 3, comprising the steps of:
   (a) introducing a powder sample into the central cavity of the helical spring;
   (b) extending the spring by the predetermined amount;
   (c) vibrating the spring in the direction normal to the length of the spring to thereby discharge a fraction of the powder sample between coils of the spring; and
   (d) measuring the at least one vibration characteristic of the spring in order to determine the mass of the discharged fraction of the powder sample.

11. A method according to claim 10, wherein the step (d) comprises determining the mass of powder remaining in the central cavity based on the at least one measured vibration characteristic, and determining the mass of the discharged fraction based on the mass of the powder remaining in the central cavity.

12. A particle size distribution analyzer according to claim 1, wherein the spring is supported such that the length of the spring is generally horizontal.

13. A particle size distribution analyzer according to claim 1, wherein the spring is supported such that the length of the spring is generally vertical.

14. A particle size distribution analyzer according to claim 1, wherein the spring is supported such that the length of the spring is vertically inclined.

15. A particle size distribution analyzer according to claim 1, further including control means positioned within the spring to limit lateral deflection of the spring.

16. A particle size distribution analyzer according to claim 1, further including control means positioned outside the spring to limit lateral deflection of the spring.

17. A particle size distribution analyzer according to claim 1, wherein the vibration generator is mechanically linked to the spring.

18. A particle size distribution analyzer according to claim 1, wherein the spring is made of magnetic material, and the vibration generator comprises an electromagnet generating a varying magnetic field in which the spring is placed.

19. A method of using the particle size distribution analyzer of claim 1, comprising the steps of:
   (a) introducing a powder sample into the central cavity of the helical spring;
   (b) extending the spring by a first predetermined amount;
   (c) vibrating the spring in the direction normal to the length of the spring to thereby discharge a first fraction of the powder sample between coils of the spring; and
   (d) measuring the mass of the first discharged fraction of the powder sample.

20. A method according to claim 19, further including the steps of:
   (e) extending the spring by a further predetermined amount;
   (f) vibrating the spring in the direction normal to the length of the spring to thereby discharge an additional fraction of the powder sample between the coils of the spring; and
   (g) measuring the mass of the additional discharged fraction of the powder sample.

21. A method according to claim 20, wherein steps (e), (f) and (g) are repeated until the powder sample is ceases to be discharged from the central cavity of the spring.

22. A method according to claim 21, further comprising the step of determining particle size distribution based on the measured mass of the respective discharged fractions of the powder sample.

23. A particle size distribution analyzer according to claim 1, further comprising a support structure for supporting the helical spring, and wherein the means for measuring the mass of the discharged powder comprises means for measuring at least one vibration characteristic of the support structure and means for determining the mass of powder remaining in the central cavity based on the at least one measured vibration characteristic.

24. A particle size distribution analyzer according to claim 23, wherein the means for measuring the mass of the discharged powder comprises means for measuring an amplitude of vibration of the support structure.

25. A particle size distribution analyzer according to claim 24, wherein the means for measuring the mass of the discharged powder comprises a feedback circuit which includes the support structure therein and which controls the vibration generator to vibrate the support structure at a resonant frequency.

26. A particle size distribution analyzer according to claim 24, wherein the means for measuring the mass of the discharged powder comprises a manually tunable circuit for controlling the vibration generator to vibrate the support structure at a resonant frequency.

27. A particle size distribution analyzer according to claim 23, wherein the means for measuring the mass of the discharged powder comprises means for measuring a resonant frequency of vibration of the support structure.

28. A particle size distribution analyzer according to claim 27, wherein the means for measuring the mass of the discharged powder comprises a feedback circuit which includes the support structure therein and which controls the vibration generator to vibrate the support structure at the resonant frequency.

29. A particle size distribution analyzer according to claim 27, wherein the means for measuring the mass of the discharged powder comprises a manually tunable circuit for measuring a frequency of the support structure at resonance.

30. A method of using the particle size distribution analyzer of claim 23, comprising the steps of:
   (a) introducing a powder sample into the central cavity of the helical spring;
   (b) extending the spring by the predetermined amount;
   (c) vibrating the spring in the direction normal to the length of the spring to thereby discharge a fraction of the powder sample between coils of the spring; and
   (d) measuring the at least one vibration characteristic of the support structure in order to determine the mass of the discharged fraction of the powder sample.

31. A method according to claim 30, wherein the step (d) comprises determining the mass of powder remaining in the central cavity based on the at least one measured vibration characteristic, and determining the mass of the discharged fraction based on the mass of the powder remaining in the central cavity.

* * * * *

UNITED STATES PATENT AND TRADEMARK OFFICE
CERTIFICATE OF CORRECTION

PATENT NO. : 6,072,308
DATED : June 6, 2000
INVENTOR(S) : Haruon Margerefteh et al.

Page 1 of 1

It is certified that error appears in the above-identified patent and that said Letters Patent is hereby corrected as shown below:

<u>Title page,</u>
Item [56] References Cited under "U.S. Patent Documents",
insert -- 1,450,145  3/1923  Ellenwood.....209/234 --.

Signed and Sealed this

Fourth Day of December, 2001

Attest:

*Nicholas P. Godici*

Attesting Officer

NICHOLAS P. GODICI
*Acting Director of the United States Patent and Trademark Office*